United States Patent [19]

Mauch

[11] 4,167,121

[45] Sep. 11, 1979

[54] PRECISION ULTRASONIC EVALUATION AND RECORDING SYSTEM

[75] Inventor: John W. Mauch, Danville, Calif.

[73] Assignee: The United States of America as represented by the Secretary of the Navy, Washington, D.C.

[21] Appl. No.: 903,431

[22] Filed: May 8, 1978

[51] Int. Cl.² ............................................. G01N 29/04
[52] U.S. Cl. ....................................................... 73/640
[58] Field of Search ......................... 73/640, 622, 618

[56] References Cited

U.S. PATENT DOCUMENTS

| | | | |
|---|---|---|---|
| 3,350,925 | 11/1967 | Coy | 73/640 |
| 3,552,190 | 1/1971 | Lefebvre | 73/622 |
| 3,894,425 | 7/1975 | Winters et al. | 73/640 |
| 3,981,184 | 9/1976 | Matay | 73/622 |

Primary Examiner—Anthony V. Ciarlante
Attorney, Agent, or Firm—R. S. Sciascia; Charles D. B. Curry

[57] ABSTRACT

A precision ultrasonic evaluation and recording system is provided which uses immersed ultrasonics for locating and inspecting structural integrity flaws in general metal cylinders, expecially warheads, and for recording point-to-point structural integrity flaw information.

8 Claims, 5 Drawing Figures

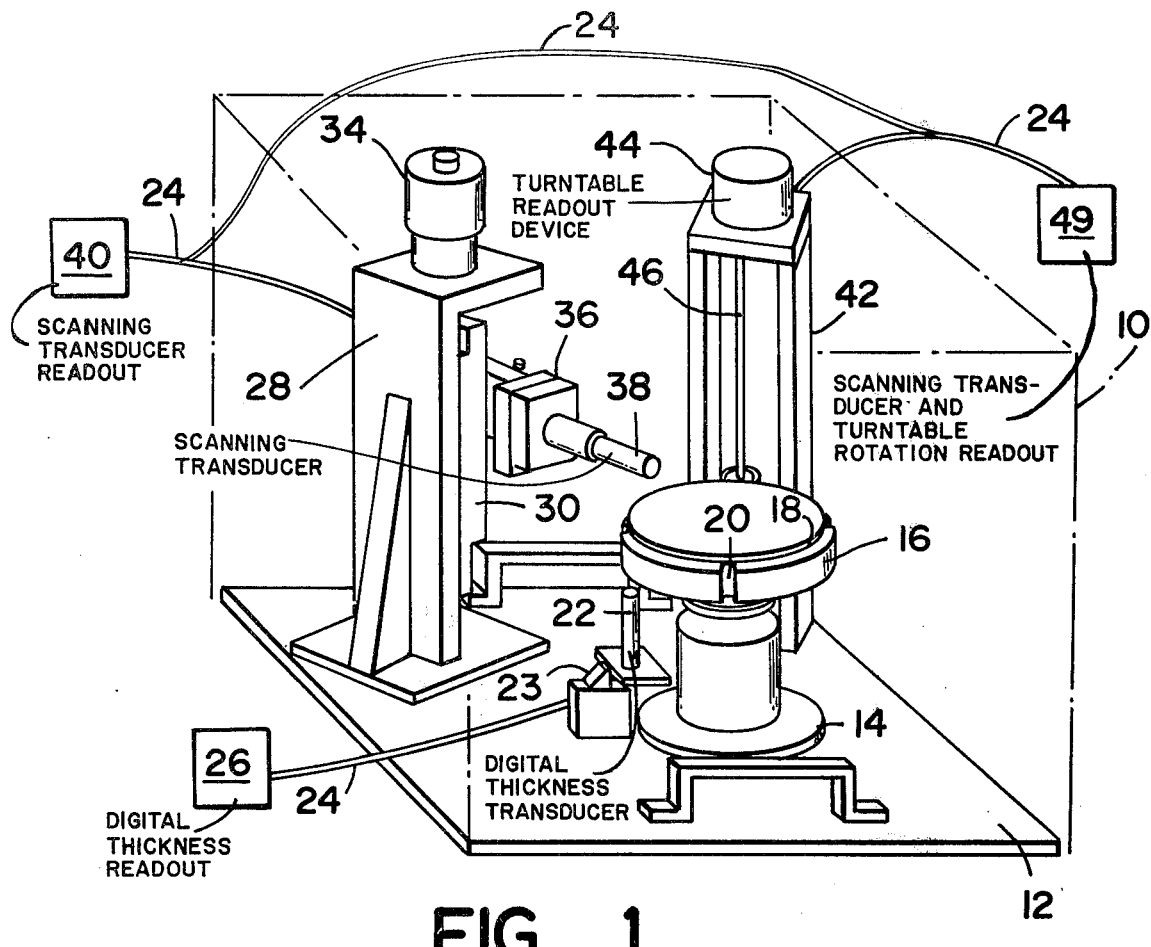
FIG_1
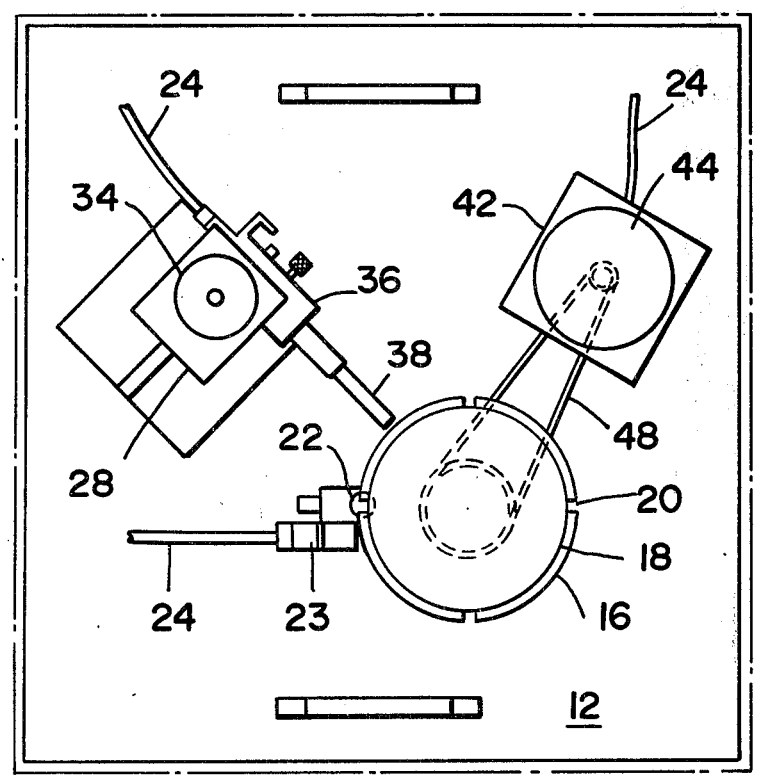
FIG_2

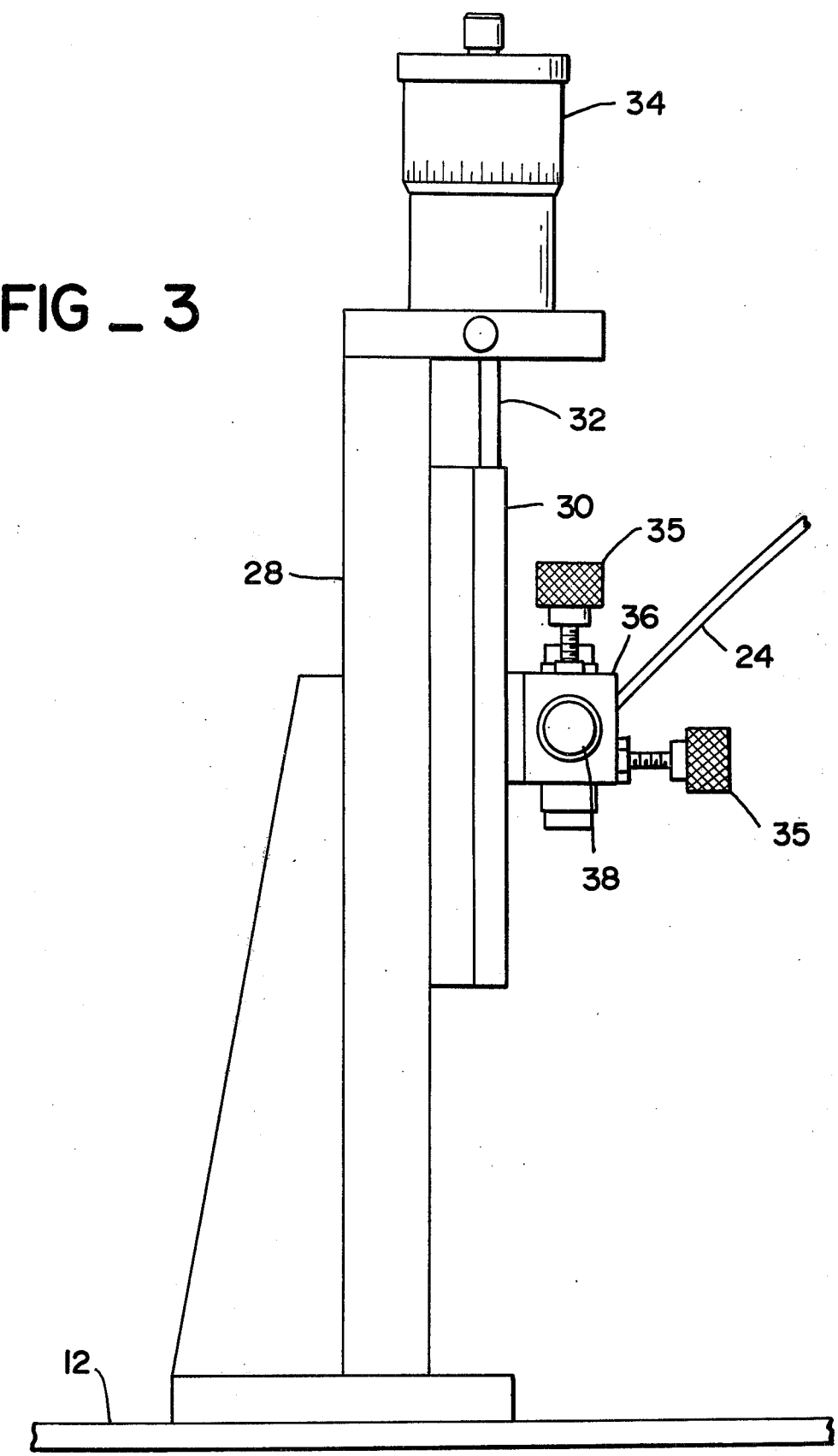
FIG_3

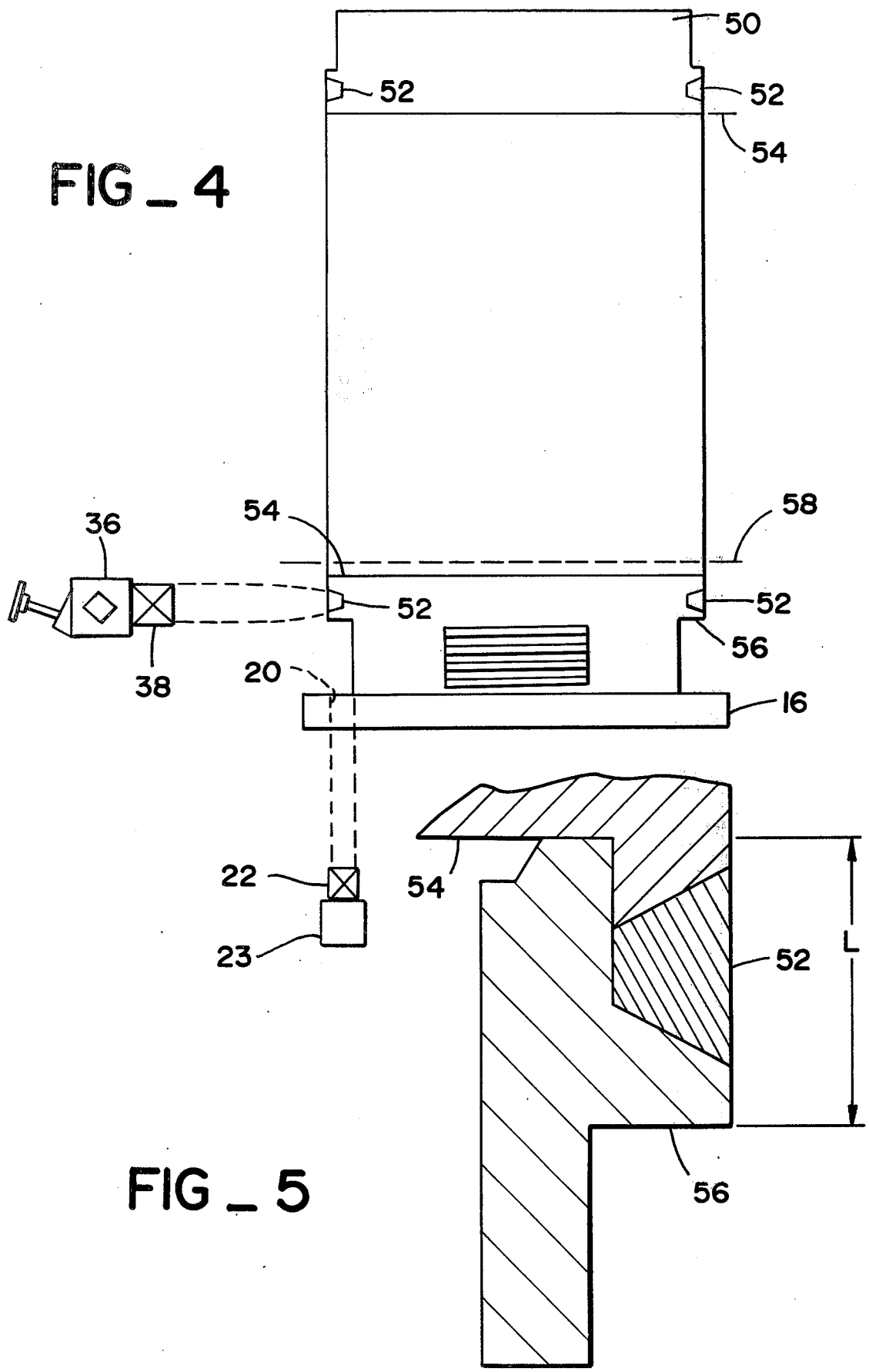

PRECISION ULTRASONIC EVALUATION AND RECORDING SYSTEM

BACKGROUND OF THE INVENTION

1. Field of the Invention

This invention relates to non-destructive testing apparatus. More specifically, this invention relates to ultrasonic test and evaluation of general metal cylinders. In particular, the invention relates to an ultrasonic testing and evaluation device for inspecting the SPARROW MK 71/38 warheads.

2. Description of the Prior Art

For several years, the United States Navy has had the problem of being unable to adequately detect critical flaws in the structural integrity of various warheads, especially the SPARROW MK 71/38 warheads. The flaws most commonly occur in the peripheral weldments. These peripheral weldments are critical since they must sustain the high loading forces caused by aircraft launch and by numerous captive flight takeoffs and landings.

Flaw detection was first attempted employing the contact inspection procedure. In this, a hand-held transducer was placed on or about the weldment and then moved about the periphery of the warhead to detect flaws in the peripheral weldments. Since the outer surface of the cylindrical warhead is machined after welding, both initial placement of the transducer and subsequent movement along the approximate line of the weldment were subject to relatively large error. This procedure was limited to detection of total disbondment of the weld.

A second flaw detection approach was employed in which the transducer was suspended on a long, flexible search tube. This tube, however, was adversely affected by vibrations in the water surrounding the test apparatus and the cylinder to be tested. These vibrations were generated by initial immersion of the cylinder in the water; by external disturbances transmitted to the test support stand; and by movement of the search tube itself within the water as it traced the weldment boundary. This limited such instruments to detection of flaws of 0.010 inch or greater. Such tolerances were and are unacceptable for the detection of critical flaws in the structural integrity of the warheads. A device was needed having the capability to detect and evaluate flaws with 0.005 inch accuracy and to provide a permanent record of the test results. The instant invention is directed to that need.

Although the instant invention is used to inspect peripheral weldments on forward and aft ends of the SPARROW MK 71/38 warheads, it has the capability to provide extremely accurate detection and recording on general metal cylinders having solid or axially laminate construction. Employment of the instant invention to such general metal cylinders would be obvious to one skilled in the art of non-destructive testing.

SUMMARY OF THE INVENTION

The instant invention provides a precise ultrasonic evaluation and recording system using immersed ultrasonics for locating and inspecting structural integrity flaws in general metal cylinders, especially warheads, and for permanently recording point-to-point flaw information.

It is a primary object of the invention to provide an apparatus for non-destructive testing general metal cylinders by means of immersed ultrasonics and to further provide a permanent data record of the test results.

It is a further object of the invention to provide an apparatus for ultrasonically locating and testing the peripheral weldments of SPARROW MK 71/38 warheads.

Still another object of the invention is to provide an ultrasonic testing apparatus having capability to locate, test and record information on structural integrity flaws to 0.005 inch accuracy.

Other objects, advantages and novel features of the invention will become apparent from the following detailed description of the invention when considered in conjunction with the accompanying drawings wherein:

BRIEF DESCRIPTION OF THE DRAWINGS

FIG. 1 illustrates a sight elevation view of the ultrasonic test apparatus;

FIG. 2 illustrates a plan view of the test apparatus;

FIG. 3 is an enlarged view of the vertical support stand and scanning transducer;

FIG. 4 illustrates a schematic relationship between the two transducers and the cylinder to be tested;

FIG. 5 is a cross-sectional view of the warhead to be tested and the critical area to be scanned.

DESCRIPTION OF THE PREFERRED EMBODIMENT

Referring to FIGS. 1 and 2, a lucite tank 10, open at one end, is placed on a bench support, not shown, and a brass base plate 12 placed inside. The brass base plate 12 has two handles for lifting it and a plurality of threaded holes, not shown, for variable positioning of the ultrasonic testing components. A brass turntable 14 upon which the cylinders to be examined, not shown, will be placed is attached to the base plate 12. The upper portion of the turntable 4 is a thick rotating disk 16 having a circumferential groove 18 which serves as a receptacle for the cylinders to be examined and four slots 20, only one shown, bored through the outer edge of and located at 90° intervals on the circumference of the disk 16. A digital thickness transducer 22 is attached to the base plate 12 such that ultrasonic energy may be transmitted through the slots 20 sequentially upon rotation of the disk 16. An output signal from the digital thickness transducer 22 is transmitted by electrical cable 24 to a digital thickness readout 26. A brass vertical support stand 28 is affixed to the base plate 12 and positioned according to the size of the cylinder to be examined. A brass dove-tailed slide 30 is connected to the support stand 28 and a vertical positioning shaft 32, shown in FIG. 3, which in turn is connected to a micrometer 34. Rotation of the micrometer 34 causes precise, small-scale motion of the dove-tail slide 30 along the positioning shaft 32. Mounted on the dove-tail slide 30 is a mini-manipulator 36 on which is affixed a scanning transducer 38 used to locate/inspect structural integrity flaws in the cylinder, not shown. An electrical cable 24 transmits an electrical output signal from the scanning transducer 38 to a scanning transducer readout 40 amd a hard-copy readout 49. A second brass vertical support structure 42 is attached to base plate 12 and supports a turntable readout device 44 as well as enclosing an extending brass center shaft 46 from the turntable readout device 44. A coupling chain 48 connects the turntable 14 to the center shaft 46 such that rotation of the turntable 14 causes a rotation of the center shaft 46 which produces an output signal from the turntable readout device 44. The output signal is transmitted by electrical cable 24 to a turntable rotation readout 49.

Referring to FIG. 3, positioning controls 35 affixed to the mini-manipulator 36 properly orient the scanning transducer 38 such that the emitted ultrasonic energy beam is normal to the surface of the cylinder, not shown, to be inspected.

Referring to FIG. 4, the digital thickness transducer 22 beams ultrasonic energy through a slot 20 in the turntable disk 16 to provide vertical positioning information for the scanning transducer 38 such that it may inspect a specific plane section of the cylindrical warhead 50. In the instant case, this plane section is the peripheral weldment 52 of the rod-bundle ends 54, only one end shown, of a warhead to the thread-seat surface 56, only one end shown, of the warhead. During scanning operation, the scanning transducer 38 and the peripheral weldment 52 are immersed in water 58 which partially fills the lucite tank 10 and acts to couple the ultrasonic energy between the scanning transducer 38 and the weld area 52.

In FIG. 5 is shown an enlarged cross-section view of the weld area 52, the rod-bundle ends 54, and the thread-seat surface 56. The digital thickness transducer 22 precisely determines the critical spacing of these regions, denoted by L, such that the scanning transducer 38 may be properly positioned.

The instant invention has been used to inspect the forward and aft weld surfaces on SPARROW MK 71/38 warheads and an example of that test procedure is set forth below. However, use of the instant invention can easily be extended to inspect other general cylinders and it is not, therefore, confined solely to the example given.

Example of Operation

The digital thickness transducer 22 must first be aligned and calibrated. The lucite tank 10 is filled with water such that the water level 58 lies above the weld area 52 to be inspected. A reference standard similar to the warheads to be tested is placed on disk 16 and engaging groove 18. The standard has a forward and aft circular plate corresponding to the design location of the forward and aft weld surfaces of the warhead to be inspected. Further, each plate has two notches machined into it, one corresponding to a defective weld and one corresponding to a proper weld. When the standard is properly placed on the disk 16, the reference weld notches do not lie above the slots 20 in the disk 16. The digital thickness transducer 22 is then positioned below the standard such that its emitted energy beam passes through one of the slots 20 in the disk 16 and is normal to the base of the standard. The mini-manipulator 23 is then used to adjust the transducer 22 until a maximum echo signal is observed on the digital thickness readout 26. The transducer 22 is then locked into place. The reference standard is then removed and a first thickness standard having known thickness less than the location of the interface between the rod-bundle 54 and the thread-seat surface 56 is placed over the slot 20 above the transducer 22. The digital thickness readout is adjusted to read this thickness value to ±0.001 inch. The procedure is then repeated for a second thickness standard having known thickness greater than the location of the interface between the rod-bundle 54 and the thread-seat surface 56. The digital thickness transducer is now aligned and calibrated to read linearly over the expected range of locations of the surface weld area constituting the described interface.

The scanning transducer 38 is then aligned and calibrated using the two reference notches machined into the standard corresponding to the weld surface to be inspected. The vertical support stand 28 is previously adjusted to bring the water path distance between the scanning transducer 38 and the reference standard to about two inches. The dovetail slide 30, the micrometer 34, and the mini-manipulator 36 are then used to point the scanning transducer 38 normal to the surface of the reference standard and precisely at the weld surface area, the interface described above, to be examined. Such positioning information is taken from the weld locating data obtained from the digital thickness readout 26. Air bubbles, if any, are then removed from the area about the weld surface. The scanning transducer readout 40 is then adjusted such that test measurement readings will be taken from the outer surface of the cylinder inwards toward the longitudinal axis of the cylinder. The electronic signal corresponding to this radial region is called the flaw gate of the scanning transducer readout 40. The reference standard is then rotated such that the notch corresponding to a defective weld is directly in front of the transducer 38 and the echo signal from that notch is adjusted to be about 80±5% of full scale readout in the scanning transducer readout 40. Similarly, the notch corresponding to the good weld is positioned in front of the scanning transducer 38 and its echo signal is adjusted to be about 50±10% of full scale readout on the scanning transducer readout 40. The actual values recorded on readout device 40 for notch 1 and notch 2 are then averaged and a compensation or delta factor is added to the average. Such a delta factor may be stamped on the reference standard for use in the inspection process. A reject signal level is then marked on the scanning readout 40 and an internal alarm set equal to the averaged notch signal values plus the delta factor. The system is now calibrated and a peripheral weldment may be inspected on a warhead.

A warhead is lowered onto the disk 16 such that it engages groove 18 and the interface described above is precisely located employing the digital thickness transducer 22 and the digital thickness transducer readout 26. The micrometer 34 is then used to position the scanning transducer 38 such that it is pointed precisely at the interface making up the peripheral weldment. Positioning information is taken from the digital thickness readout 26. The warhead is then rotated such that a circumferential scan of the peripheral weldment is made by the scanning transducer 38 and the results displayed on the scanning transducer readout 40. Any return signal falling within the gated area and above the reject level described supra triggers a flaw alarm contained in the scanning transducer readout 40. Scanning transducer signal output is sent to a hard-copy readout 49 which also records turntable rotation derived by means of a coupling chain 48 between the turntable 14 and a center shaft 46 of a potentiometer 44 yielding turntable rotation readout signals. Thus, circumferential length is recorded on the x-axis and scanning transducer output is recorded on the y-axis of the hard-copy recorder 49.

Obvious extensions and modifications to the present system are suggested to a practitioner skilled in the ultrasonic testing art in light of the above teachings. Such extensions and modifications are contemplated and are within the scope of the appended claims.

What is claimed is:

1. A precision ultrasonic evaluation and recording system comprising:
   (a) means for rotatably retaining general metal cylinders, said cylinders to be ultrasonically inspected for structural integrity flaws;
   (b) means for vertically locating circular sections in said general metal cylinders by beaming ultrasonic energy perpendicularly into said general metal cylinder along its longitudinal axis, said locating means positioned below said retaining means and said metal cylinder;
   (c) first means connected to said locating means for digitally displaying said vertical location of said circular section within said general metal cylinder;
   (d) means for scanning said circular section for structural flaws, said scanning means intermittently emitting a beam of ultrasonic energy normal to the surface of said general metal cylinder and receiving ultrasonic flow detection information as said general metal cylinder is rotated by said rotatable retaining means;
   (e) means for vertically positioning said scanning means;
   (f) second means connected to said scanning means for displaying said flaw detection information;
   (g) means connected to said retaining means for generating an electrical signal proportional to degree of rotation of said retaining means;
   (h) third means connected to the output of said scanning means and said generating means for recording permanent inspection test results; and
   (i) a tank for enclosing said retaining means, said locating means, said scanning means and said generating means for immersion in a liquid medium.

2. An ultrasonic evaluation and recording system as recited in claim 1 wherein said retaining means includes:
   (a) a brass turntable having a thick flat disk upon which said general metal cylinders are placed; and
   (b) a circumferential groove in said disk for engaging said general metal cylinders.

3. An ultrasonic evaluation and recording system as recited in claim 2 wherein said disk has at least one bore through the disk, said bore located in the circumference of said disk and capable of alignment with said beam of ultrasonic energy emitted by said locating means.

4. An ultrasonic evaluation and recording system as recited in claim 1 wherein said locating means includes:
   (a) an ultrasonic transducer; and
   (b) means for orienting said ultrasonic transducer such that its longitudinal axis is normal to the bottom surface of said disk.

5. An ultrasonic evaluation and recording system as recited in claim 1 wherein said scanning means includes:
   (a) an ultrasonic transducer; and
   (b) means for anglulating said ultrasonic transducer such that its longitudinal axis is normal to the bottom surface of said disk.

6. An ultrasonic evaluation and recording system as recited in claim 1 wherein said vertical positioning means includes:
   (a) first brass support stand, said stand having a bore through its upper end;
   (b) a micrometer mounted on top of said first support stand and having its vertical axis alinged with the center of said bore;
   (c) a vertically mounted adjusting shaft connected to said micrometer and extending through said bore to the base of said first support stand; and
   (d) a dovetail slide connected to said vertical first support stand and said adjusting shaft such that rotation of said micrometer causes movement of said dovetail slide along said first vertical support stand and said adjusting shaft; said angular means affixed to said dovetail slide.

7. An ultrasonic evaluation and recording system as recited in claim 1 wherein said turntable rotation signal generating means includes:
   (a) a brass vertical support stand having an aperture in its upper surface;
   (b) a potentiometer mounted on top of said vertical support stand and over said aperture such that the vertical axis of said potentiometer is aligned with the center of said aperture; and
   (c) a vertically mounted rotating shaft connected to said potentiometer, connected to the base of said vertical support stand and coupled to said rotating means such that rotation of said rotating means produces a corresponding rotation of said rotating shaft causing the potentiometer to transmit an electrical signal corresponding to amount of rotation of said turntable.

8. A precision ultrasonic evaluation and recording system comprising:
   (a) means for rotatably retaining general metal cylinders for ultrasonic inspection;
   (b) means for ultrasonically determining longitudinal location of circular sections of interest in said general metal cylinders said determining means having a visual information display of said vertical location;
   (c) means for ultrasonically evaluating structural integrity of said circular sections, said evaluating means positioned outside and normal to the surface of said general metal cylinder by using said visual information display from said determining means and outputting a signal corresponding to said structural integrity of said circular section;
   (d) means for correlating said output signal from said evaluating means with peripheral location on said general metal cylinder, said correlating means connected to said retaining means and outputting a signal corresponding to degree of rotation of said retaining means; and
   (e) recording means connected to and receiving said output signals of said evaluating means and said correlating means for permanently recording output from said evaluating means and said correlating means.

* * * * *